(12) United States Patent
Zamore

(10) Patent No.: US 7,728,049 B2
(45) Date of Patent: *Jun. 1, 2010

(54) IRRADIATION CONVERSION OF THERMOPLASTIC TO THERMOSET POLYMERS

(76) Inventor: Alan M. Zamore, 23 Mountain Ave., Monsey, NY (US) 10952

( * ) Notice: Subject to any disclaimer, the term of this patent is extended or adjusted under 35 U.S.C. 154(b) by 0 days.

This patent is subject to a terminal disclaimer.

(21) Appl. No.: 10/608,026

(22) Filed: Jun. 30, 2003

(65) Prior Publication Data

US 2004/0002729 A1 Jan. 1, 2004

Related U.S. Application Data

(63) Continuation-in-part of application No. 08/947,000, filed on Oct. 8, 1997, now Pat. No. 6,596,818, which is a continuation-in-part of application No. 08/727,145, filed on Oct. 8, 1996, now Pat. No. 5,900,444.

(51) Int. Cl.
  C08J 3/28 (2006.01)
  C08J 3/24 (2006.01)
  C08F 283/02 (2006.01)
  C08F 283/04 (2006.01)
  C08F 283/06 (2006.01)

(52) U.S. Cl. .................. 522/134; 2/159; 2/161.7; 36/25 R; 36/32 R; 128/844; 399/350; 522/135; 522/136; 522/137; 522/138; 522/139; 522/140; 522/141; 522/142; 522/144; 522/164; 525/426

(58) Field of Classification Search ............... 522/134, 522/135, 136, 137, 138, 139, 140, 141, 164, 522/142, 144; 525/164, 426; 2/159, 161.7; 36/25 R, 32 R; 128/844; 399/350; 604/96.01, 604/103.11, 264, 349, 523, 532, 915; 606/7, 606/228, 231

See application file for complete search history.

(56) References Cited

U.S. PATENT DOCUMENTS

| | | | |
|---|---|---|---|
| 3,616,364 A | 10/1971 | D'Alelio | |
| 3,642,964 A | 2/1972 | Rausch et al. | |
| 3,658,670 A | 4/1972 | Holicky et al. | |
| 3,674,743 A | 7/1972 | Verdol et al. | |
| 3,719,539 A | 3/1973 | Lamb et al. | |
| 3,871,908 A | 3/1975 | Spoor et al. | |
| 4,013,806 A | 3/1977 | Volkert et al. | |
| 4,025,407 A | 5/1977 | Chang et al. | |
| 4,065,589 A * | 12/1977 | Lenard et al. | 428/34.7 |
| 4,101,699 A | 7/1978 | Stine et al. | |
| 4,133,731 A | 1/1979 | Hansen et al. | |
| 4,151,057 A | 4/1979 | St. Clair et al. | |
| 4,255,552 A | 3/1981 | Schollenberger et al. | |
| 4,264,658 A * | 4/1981 | Tobias et al. | 427/518 |
| 4,266,005 A | 5/1981 | Nakamura et al. | |
| 4,289,682 A | 9/1981 | Peters | |
| 4,331,697 A | 5/1982 | Kudo et al. | |
| 4,342,793 A | 8/1982 | Skinner et al. | |
| 4,358,354 A | 11/1982 | Iida et al. | |
| 4,443,588 A | 4/1984 | Fukuda et al. | |
| 4,444,816 A * | 4/1984 | Richards et al. | 428/34.9 |
| 4,552,815 A | 11/1985 | Dreher et al. | |
| 4,567,083 A | 1/1986 | Arioka et al. | |
| 4,607,084 A | 8/1986 | Morris | |
| 4,654,233 A | 3/1987 | Grant et al. | |
| 4,687,689 A | 8/1987 | Yazaki et al. | |
| 4,762,884 A | 8/1988 | Goyert et al. | |
| 4,820,782 A | 4/1989 | Ueno | |
| 4,871,811 A | 10/1989 | Gaku et al. | |
| 4,897,433 A | 1/1990 | Sugo et al. | |
| 4,948,859 A | 8/1990 | Echols et al. | |
| 5,053,316 A * | 10/1991 | Suzuki et al. | 430/281.1 |
| 5,084,529 A | 1/1992 | Crano | |
| 5,109,097 A | 4/1992 | Klun et al. | |
| 5,116,652 A | 5/1992 | Alzner | |
| 5,236,978 A | 8/1993 | Selvig et al. | |
| 5,266,669 A | 11/1993 | Onwunaka et al. | |
| 5,284,883 A | 2/1994 | Ueno et al. | |
| 5,328,940 A | 7/1994 | Zimmer | |
| 5,334,201 A | 8/1994 | Cowan | |
| 5,336,585 A | 8/1994 | Takahashi et al. | |
| 5,374,704 A | 12/1994 | Müller et al. | |
| 5,382,633 A | 1/1995 | Scott et al. | |
| 5,438,106 A | 8/1995 | Siranovich et al. | |
| 5,442,036 A | 8/1995 | Beavers et al. | |
| 5,455,308 A | 10/1995 | Bastiaansen | |
| 5,478,320 A * | 12/1995 | Trotta | 604/103.06 |
| 5,554,120 A * | 9/1996 | Chen et al. | 604/96.01 |
| 5,576,072 A | 11/1996 | Hostettler et al. | |
| 5,733,496 A | 3/1998 | Avellanet | |
| 5,765,682 A * | 6/1998 | Bley et al. | 206/363 |

(Continued)

FOREIGN PATENT DOCUMENTS

WO    WO 98/15199    4/1998

OTHER PUBLICATIONS

G. Beyer et al.(1992) "Radiation Crosslinked Thermoplastic Polyurethane.", International Polymer Science and Technology, (1992), pp. T/6-T/9 vol. 19 (1).

E.P. Kohler et al. (1927) American Chemical Society, vol. 49, p. 3181.

*Primary Examiner*—Rabon Sergent

(57) ABSTRACT

Disclosed is a radiation-crosslinkable thermoplastic polymer composition, a process for the preparation thereof, an angioplasty balloon and a medical catheter made using such a composition. The composition contains a reactive monomer cross-linker facilitates cross-linking of the reaction product upon contact of the cross-linker-containing composition with energy from a radiation source.

25 Claims, No Drawings

U.S. PATENT DOCUMENTS

| | | | |
|---|---|---|---|
| 5,779,729 A | 7/1998 | Severini | |
| 5,900,444 A * | 5/1999 | Zamore | 522/137 |
| 5,993,415 A * | 11/1999 | O'Neil et al. | 604/96.01 |
| 5,998,551 A * | 12/1999 | O'Neil et al. | 525/426 |
| 6,500,148 B1 * | 12/2002 | Pinchuk et al. | 604/103.11 |
| 6,592,550 B1 * | 7/2003 | Boatman et al. | 604/103.06 |
| 6,596,818 B1 * | 7/2003 | Zamore | 525/426 |
| 2002/0018866 A1 * | 2/2002 | Lee et al. | 428/36.8 |
| 2004/0092868 A1 * | 5/2004 | Murray, III | 604/103.04 |

* cited by examiner

IRRADIATION CONVERSION OF THERMOPLASTIC TO THERMOSET POLYMERS

CROSS REFERENCE TO RELATED APPLICATION

This application is a Continuation-In-Part of U.S. application Ser. No. 08/947,000 filed Oct. 8, 1997, now U.S. Pat. No. 6,596,818 issued Jul. 22, 2003 which is a Continuation-In-Part of U.S. application Ser. No. 08/727,145, filed on Oct. 8, 1996, now U.S. Pat. No. 5,900,444 issued May 4, 1999.

FIELD OF THE INVENTION

This invention relates generally to the conversion of thermoplastic polymers into thermoset polymers and more specifically to such thermoset polymers exhibiting improved physical and chemical properties, relative to the corresponding thermoplastic polymers. Illustrative of such polymers are the polyurethane thermoplastic polymers, the co-polyester elastomer thermoplastic polymers, and the nylon elastomer thermoplastic polymers all of which can be advantageously converted to thermoset forms in the presence of a reactive monomer crosslinker and actinic radiation.

BACKGROUND OF THE INVENTION

Thermoplastic polymers, are relatively easy to process into a wide variety of fabricated products. Unfortunately, however, for many of these thermoplastic polymers, the high temperature stability, and their physical properties such as mechanical strength at elevated temperatures, as well as their stability in some commonly-used organic solvents, are less than might be desired. Accordingly, methodology has been previously developed to provide heat-induced crosslinking to convert certain thermoplastic polymers, such as thermoplastic polyurethanes, into thermoset polyurethanes having the desired stability at high temperatures and in the presence of solvents. By way of illustration, U.S. Pat. No. 4,255,552 discloses thermoset polyurethane elastomers obtained by adding organic peroxides to a liquid polyurethane-forming composition prior to reacting the composition to form the polyurethane. The '552 patent teaches that a liquid polyurethane-forming composition containing "unactivated hydrogen peroxide" may be formed in a mold into a desired article and then heated to solidify and thermoset the article, or a composition in solid form such as sheet, crumbs, or granules containing "unactivated hydrogen peroxide" may be provided which are can then be formed into a desired article that is then thermoset by heating the article in a press. The organic peroxides disclosed in the '552 patent are said to have a half-life of greater than one hour at 100 deg C. Unfortunately, these peroxide-containing compositions are less stable than might be desired or necessary for a thermoplastic process such as extrusion or molding. The peroxide containing polyurethane composition would most likely thermoset prior to forming the desired finished article, thus providing technology that is not commercially practical for thermoplastics.

An alternative to heat induced crosslinking of thermoplastics into thermosets by irradiation is known in the art. For example, a technical journal article entitled "Radiation Crosslinked Thermoplastic Polyurethane", published in the journal *International Polymer Science and Technology*, Vol. 19, No. 1, pp. T/6-T/9 (1992), discloses the production of a thermoset polyurethane by using a polyisocyanate and methacrylate monomer as a radiation-cross-linkable monomer. This technical journal article does not disclose the particular polyisocyanate used in making polyurethanes disclosed therein. Further, not all polyisocyanates perform alike in irradiation-crosslinking of TPUs.

Another example is U.S. Pat. No. 4,762,884 issued Aug. 9, 1988 for "Process for the Production of Radiation-Crosslinked Thermoplastic Polyurethanes". This patent discloses the use of a cross-linking agent being a monomeric acrylate or methacrylate.

In view of the above, there is a continuing need in the polymers manufacturing community for new thermoplastic polymer compositions that can be readily thermoset by cross-linking when desired. Such compositions would provide advantageous processing capability, such as by extrusion, when the composition is in the thermoplastic state, and advantageous elevated temperature stability, solvent resistance and other enhanced properties when the composition is thermoset after formation into the desired product. Moreover, new uses for compositions known to be cross-linkable in the presence of irradiation, would also be desirable. The present invention provides such desirable polymer compositions, together with processes for the production of the composition, as well as new uses for compositions known to be irradiation cross-linkable.

SUMMARY OF THE INVENTION

In one aspect, the present invention relates to a radiation cross-linkable medical angioplasty balloon or radiation cross-linkable medical catheter made from a thermoplastic cross-linkable composition, said thermoplastic cross-linkable composition comprising:

(a) a thermoplastic polymer which is the reaction product of an aromatic polyisocyanate and a polyahl; and (b) a monomer crosslinker selected from the group consisting of methacrylate monomer crosslinkers and acrylate monomer crosslinkers, for conversion of at least a portion of said thermoplastic polymer to convert said portion from a thermoplastic to a thermoset state upon irradiation of said composition with energy from a radiation source.

In another aspect, the present invention relates to a radiation cross-linked medical angioplasty balloon or radiation cross-linked medical catheter made by irradiating a radiation cross-linkable medical angioplasty balloon or radiation crosslinkable medical catheter with energy from a radiation source.

In yet another aspect, the present invention relates to a radiation cross-linked medical angioplasty balloon or radiation cross-linked medical catheter made from a cross-linked composition, wherein said cross-linked composition is produced by irradiating a cross-linkable composition comprising:

(a) a thermoplastic polymer which is the reaction product of an aromatic polyisocyanate and a polyahl; and (b) a monomer crosslinker selected from the group consisting of methacrylate monomer crosslinkers and acrylate monomer crosslinkers, meta-phenylene dimaleimide, and combinations thereof; said monomer crosslinker present in said composition in an amount sufficient to cross-link at least a portion of said thermoplastic polymer to convert said portion from a thermoplastic to a thermoset state upon irradiation of said composition with energy from a radiation source.

In another aspect, the present invention relates to a radiation cross-linkable medical angioplasty balloon or radiation cross-linkable medical catheter made from a thermoplastic cross-linkable composition, said thermoplastic cross-linkable composition comprising:

(a) a thermoplastic polymer selected from the group consisting of nylon, a copolyester copolymer of poly(1,4-butanediol terephthalate) and poly(alkylene ether terephthalate), a copoly(ether-ester-amide) polymer, and copolymers of polylaurinlactam and polytetrahydrofuran, and a reaction product of an aliphatic polyisocyanate and a polyahl; and (b) a monomer cross-linker comprising acrylate monomer crosslinkers, said monomer cross-linker present in said composition in an amount sufficient to provide cross-linking of at least a portion of said thermoplastic polymer to convert said portion from a thermoplastic to a thermoset state upon irradiation of said composition with energy from a radiation source.

In yet another aspect, the present invention relates to a radiation cross-linked medical angioplasty balloon or radiation cross-linked medical catheter made from a cross-linked composition, wherein said cross-linked composition is produced by irradiating a crosslinkable composition comprising:

(a) a thermoplastic polymer selected from the group consisting of nylon, a copolyester copolymer of poly(1,4-butanediol terephthalate) and poly(alkylene ether terephthalate), a copoly(ether-ester-amide) polymer, and copolymers of polylaurinlactam and polytetrahydrofuran, and a reaction product of an aliphatic polyisocyanate and a polyahl; and (b) a monomer cross-linker comprising acrylate monomer crosslinkers, said monomer cross-linker present in said composition in an amount sufficient to cross-link at least a portion of said thermoplastic polymer to convert said portion from a thermoplastic to a thermoset state upon irradiation of said composition with energy from a radiation source.

In another aspect, the present invention invention relates to the radiation crosslinked composition made by irradiating the radiation crosslinkable composition comprising:

(a) a thermoplastic copoly(ether-ester-amide) polymer and (b) a monomer cross-linker selected from the group consisting of triallylisocyanurate ("TAIC") or triallylcyanurate ("TAC") allylic monomers, and combinations thereof, with energy from a radiation source, wherein said radiation crosslinked composition is in the form of a device selected from the group consisting of surgical gloves, angioplasty balloons, birth control sheathes, heat shrinkable tubing, heat-shrinkable film, wire and cable jackets, orthodontic ligatures, seals, gaskets, o-rings, shoe soles, toner wiper blades, medical implant devices, and coated wires.

In another aspect, the present invention relates to a device selected from the group consisting of surgical gloves, angioplasty balloons, birth control sheathes, heat shrinkable tubing, heat-shrinkable film, wire and cable jackets, orthodontic ligatures, seals, gaskets, o-rings, shoe soles, toner wiper blades, medical implant devices, and coated wires containing a radiation crosslinked composition made by irradiating the radiation crosslinkable composition comprising:

(a) a thermoplastic copoly(ether-ester-amide) polymer and (b) a monomer cross-linker selected from the group consisting of triallylisocyanurate ("TAIC") or triallylcyanurate ("TAC") allylic monomers, and combinations thereof, with energy from a radiation source.

In yet another aspect, the present invention relates to a radiation crosslinked composition made by irradiating a radiation crosslinkable composition comprising:

(a) a thermoplastic aromatic polyurethane polymer and (b) a monomer acrylic or methacrylic cross-linker, and combinations thereof, with the proviso that the monomer acrylic or methacrylic cross-linker is other than trimethylolpropane triacrylate, trimethylolpropane trimethacrylate, and triacrylformal, with energy from a radiation source, wherein said radiation crosslinked composition is in the form of heat shrinkable tubing.

In another aspect, the present invention relates to an article suitable for, sterilization by exposure to heat or, sterilization by exposure to radiation, surface modification by exposure to radiation or surface grafting by exposure to radiation, comprising a cross-linked composition, wherein said cross-linked composition is produced by irradiating a crosslinkable composition comprising:

(a) a thermoplastic polymer selected from the group consisting of nylon, a copolyester copolymer of poly(1,4-butanediol terephthalate) and poly(alkylene ether terephthalate), a copoly(ether-ester-amide) polymer, and copolymers of polylaurinlactam and polytetrahydrofuran, and a reaction product of a polyisocyanate and a polyahl; and combinations thereof, and (b) a monomer cross-linker selected from the group consisting of allylic monomer crosslinkers, methacrylate monomer crosslinkers, acrylate monomer crosslinkers, and combinations thereof; said monomer cross-linker present in said composition in an amount sufficient to cross-link at least a portion of said thermoplastic polymer to convert said portion from a thermoplastic to a thermoset state upon irradiation of said composition with energy from a radiation source, wherein the amount of crosslinked composition is sufficient to increase the radiation tolerance or heat sterilization tolerance of the article over that of the article alone without the crosslinked composition.

In another aspect, the present invention relates to an article suitable for, sterilization by exposure to heat or, sterilization by exposure to radiation, surface modification by exposure to radiation or surface grafting by exposure to radiation, comprising a cross-linkable composition, wherein said cross-linkable composition comprises:

(a) a thermoplastic polymer selected from the group consisting of nylon, a copolyester copolymer of poly(1,4-butanediol terephthalate) and poly(alkylene ether terephthalate), a copoly(ether-ester-amide) polymer, and copolymers of polylaurinlactam and polytetrahydrofuran, and a reaction product of a polyisocyanate and a polyahl; and combinations thereof, and (b) a monomer cross-linker selected from the group consisting of allylic monomer crosslinkers, methacrylate monomer crosslinkers, acrylate monomer crosslinkers, and combinations thereof; said monomer cross-linker present in said composition in an amount sufficient to provide cross-linking of at least a portion of said thermoplastic polymer from a thermoplastic to a thermoset state upon irradiation of said composition with energy from a radiation source, wherein the amount of crosslinkable composistion is sufficient to increase the radiation sterilization tolerance of the article over that of the article alone without the crosslinkable composition.

In another aspect, the present invention relates to a wholly or partially encapsulated device, wholly or partially encapsulated with a cross-linkable composition, wherein said cross-linked composition is produced by irradiating a crosslinkable composition comprising:

(a) a thermoplastic polymer selected from the group consisting of nylon, a copolyester copolymer of poly(1,4-butanediol terephthalate) and poly(alkylene ether terephthalate), a copoly(ether-ester-amide) polymer, and copolymers of polylaurinlactam and polytetrahydrofuran, and a reaction product of a polyisocyanate and a polyahl; and combinations thereof, and (b) a monomer cross-linker selected from the group consisting of allylic monomer crosslinkers, methacrylate monomer crosslinkers, acrylate monomer crosslinkers, and combinations thereof; with the proviso that for the reaction product of a polyisocyanate and a polyahl the monomer acrylic or methacrylic cross-linker is other than trimethylolpropane triacrylate, trimethylolpropane trimethacrylate, and triacrylformal, said monomer cross-linker present in said composition in an amount sufficient to provide cross-linking of at least a portion of said thermoplastic polymer from a thermoplastic to a thermoset state upon irradiation of said composition with energy from a radiation source, and wherein the crosslinked encapsulation composition is expanded to a larger size than the device to be encapsulated, by a heating and forming process, and then cooled to retain the expanded size, said expanded crosslinked encapsulation composition possessing the characteristic of "memory" due to the crosslinked polymer comprising the crosslinked encapsulation composition, and wherein the medical device to be wholly or partially encapsulated is placed within the expanded shaped object with "memory", and wherein heat is applied to cause the expanded crosslinked encapsulation composition with "memory" to contract and wholly or partially encapsulate the device within.

These and other aspects of the invention will become apparent upon reading the following detailed description.

DETAILED DESCRIPTION OF THE INVENTION

It has been found, in accordance with the present invention, that a wide variety of polymers and copolymers are suitably irradiated in the presence of specific monomeric radiation sentisizers in order to cause the polymer to crosslink, thereby enhancing the resistance of the polymer against thermal and chemical degradation caused by exposure to heat, corrosive chemicals, or radiation such as employed in sterilization processes, surface modification or grafting for medical or other devices.

Advantageously, co-polymers are employed in the compositions of the present invention, and the preferred co-polymers are so-called "block co-polymers". The block co-polymers contain discrete "hard" and "soft" regions in the polymer matrix that provide alternating aggregated and amorphous segments, respectively, by virtue of the specific combination of polymers employed in the co-polymer. Without wishing to be bound by any particular theory, it is believed that advantageous result associated with the use of block co-polymers, in accordance with the present invention, is attributable to the propensity for crosslinking induced by ionization radiation to occur primarily within the amorphous (i.e., the soft segment) matrix. Hence, the presence of the amorphous matrix in alternating regions throughout the polymer will promote the desired crosslinking throughout the polymer.

By way of background, block co-polymer-type thermoplastic elastomers exhibit the advantages of rubber-like elasticity and reversible melt transitions, thereby combining features of thermoplastics and rubbers without requiring vulcanization. These block co-polymer-type thermoplastic elastomers combine the further advantages of high melt temperature, low glass transition temperature, elasticity and thermoplasticity in one polymer. Blocks are formed by segregating each co-polymer into a specific polymer region. With proper sequencing and selection of co-polymer molecular weight, the polymer can exhibit the advantageous properties that characterize each block rather than an amalgamation of the unitized polymer. Block co-polymers are typically non random, and instead their backbone exhibits alternating sequences of hard and soft segments. "Hard" blocks reversibly self aggregate below the polymer melt temperature. Polymer tensile strength accrues from these aggregated regions within the polymer. The aggregation provided by virtue of these aggregated regions is reversible, hence these materials behave like they are thermoplastic polymers. Above the melt temperature, the polymer is a viscous liquid. This allows thermoplastic elastomers to be processed using conventional plastics processing equipment with the added advantage of recyclability of scrap that is produced during fabrication of the desired products. "Soft" blocks tend to accumulate in amorphous matrixes providing for regions of polymer elasticity at temperatures above the glass transition point.

There are distinct advantages associated with the ability to convert thermoplastic polymers, particularly block co-polymers, to thermoset polymers in accordance with the present invention. This ability to convert is particularly important since thermoplastic elastomers, in general, and block copolymers specifically, lack the wide temperature performance range of a thermoset elastomeric material, and their compression set, solvent resistance and deformation resistance are generally not as good as the values for those properties as obtained with a thermoset elastomeric material such as a rubber. These deficiencies are mitigated, or avoided entirely, by virtue of the ability to convert thermoplastic elastomers into thermoset elastomers in accordance with the present invention.

As mentioned above, conversion of a thermoplastic to thermoset polymer can be suitably effected using actinic radiation energy, such as photons, UV light, beta-particles and gamma-rays, or a combination thereof, emitted from a radiation source. Illustrative sources for such radiation energy include electron-beam machines, ultraviolet ("uv") lights, radioactive elements such as Cesium, cyclotrons, linacs and the like, and combinations thereof. Radiation crosslinking (also known as curing) to provide the thermoset polymer is suitably effected using a radiation sensitizing monomer or compound such as the allylic compounds and/or acrylates and/or methacrylates described herein.

Illustrative copolymers useful in the present invention include (1) co-polyester polymers including copolymers of poly (1,4 butanediol terephthalate) and poly(alkylene ether terephthalate) such as those trademarked under the HYTREL mark (DuPont), and (2) co-polyamide polymers including (a) copoly(ether-ester-amide) polymers and, the (b) PA12 elastomers being co-polymers of polyaurinlactam and polytetrahydrofuran all trademarked under various marks such as the VESTAMID mark (DeGussa), the PEBAX mark (Atochem) or other marks, and (3) the thermoplastic polyurethanes including those containing of aromatic or aliphatic diisocyanates hard segments and polyether, polyester, polycarbonate soft segments or soft segments consisting of silicone segments in combination with polyether, polyester, polycarbonate segents, trademarked under marks such as Pellethane (Dow), Estane (Noveon), Elastollan (BASF), or other marks, and (4) polyamides such as NYLON 12 or NYLON 11 manufactured by Atochem and others, NYLON 6 or 6,6, and other aliphatic or aromatic polyamides; and blends or combinations of the above polymers.

It has also been found, in accordance with the present invention, that these polymers or copolymers, together with a radiation-sentisizing monomer, are suitable for fabricating thermoset angioplasty balloons made using tubing composed in accordance with the present invention. These balloons exhibit excellent properties, including resistance against breakage when the balloon is expanded in a blood vessel to remove occlusions in the blood vessel. This balloon also comprises a reactive monomer, (such as an allylic monomer, acrylate monomer and/or methacrylate monomer) e.g. triallylisocyanurate ("TAIC"), triallylcyanurate ("TAC"), diallyl phthalate ("DAP"), meta-phenylene dimaleimide (MPDM), trimethyolpropane trimethacrylate (TMPTMA), and trimethyolpropane triacrylate (TMPTA) and combinations thereof, for crosslinking the copolymer. Irradiation activates the reactive monomer and causes the amorphous segments to be preferentially crosslinked to provide enhanced structural integrity to the balloon. The enhanced structural integrity of the thermoset balloon makes it resistant to overexpansion or breakeage during use of the balloon to remove blockage in the blood vessels.

As additional illustrations, the present invention is suitably employed to prepare thermoset articles possessing a "memory" such as shrink tubing. Also envisioned are medical or other devices or components that are coated or encapsulated fully or partially by surrounding the medical device with an oversized casing possessing "memory" and causing it to shrink to the medical device usually through the application of heat.

The present invention can also be suitably employed to prepare articles that exhibit increased tolerance or stability and less degradation when exposed to the radiation or heat processes used to sterilize or surface graft or surface modify a polymer substrate.

In accordance with the present invention, a preferred thermoplastic polymer, for example, a thermoplastic polyurethane (so-called "TPU") or polyurea or other polymer or co-polymer is suitably converted to a thermoset polyurethane or polyurea using a polymer-forming or preformed polymer in combination with a select reactive monomer (such as an allylic monomer, acrylate monomer and/or methacrylate monomer) that facilitates crosslinking with the polymer in the presence of irradiation. Illustratively, a polyurethane-forming or a preformed polyurethane (or a polyurea-forming or preformed polyurea) composition comprising a diisocyanate and a polyahl, or the reaction product thereof, together with a select reactive monomer (such as an allylic monomer, acrylate monomer and/or methacrylate monomer) as a crosslinking promoter, are mixed and irradiated to provide the desired thermoset product after forming the product from the extrudable solid thermoplastic polymer raw material.

Alternatively, the reactive monomer is suitably contacted with a polymer (or a polymer-forming composition for providing such polymer) selected from the group consisting of nylons or polyamides, co-polyamide polymers, a copolymer reaction product of polyaurinlactam and polytetrahydrofuran, and combinations thereof, and subsequently irradiated to provide a thermoset polymer before being formed into a finished product. Irradiating the composition causes the polymer to convert from a thermoplastic state to a thermoset state without encountering the risk of premature cross-linking that has plagued the above-discussed peroxide containing compositions in the prior art. The resulting thermoset polymer exhibits advantageous physical and chemical properties.

For example, some of the thermoset polyurethane made in accordance with the present invention can be formulated advantageously to be essentially free of discoloration often associated with prior art thermoset polyurethanes made from TPUs. The term "essentially free of discoloration", as used herein, is intended to mean that the thermoset polyurethane of the present invention advantageously exhibits essentially none (or little) of the undesirable yellow or orange discoloration that typically characterizes thermoset polyurethane resins produced in accordance with the aforementioned prior art patents.

Illustrative of one class of polymers, polyurethane, is suitably irradiated using a source of high energy radiation in order to cause cross-linking of the thermoplastic polyurethane composition to occur to convert the thermoplastic polyurethane to a thermoset polyurethane. The radiation source suitably provides the desired irradiation of the thermoplastic polyurethane.

As used herein, the term "irradiation", in the context of the present invention, is used expansively to encompass bombardment of the target thermoplastic polyurethane with photons, beta (also referred to herein as e-beam) particles, gamma rays, ultraviolet ("uv") radiation, combinations thereof, and the like, in order to effect conversion of the TPU to the desired thermoset polyurethane. Although the energy output from the radiation source to the thermoplastic polyurethane composition can vary over a wide range, it is preferred that, when using e-beam irradiation, an amount of radiation of from about 1 and about 100 Mega Rads, more preferably between 10 and 50 Mega Rads, most preferably between 10 and 20 Mega Rads, be imparted to the composition over a suitable period of time to insure that the polyurethane being irradiated does not overheat.

As used herein, the term "thermoplastic" is used in its broad sense to designate a material that is reprocessable at an elevated temperature, whereas "thermoset" designates a material that exhibits high temperature stability without such reprocessability at elevated temperatures. The term "thermoplastic elastomer" is sometime used to designate a melt processible material that possesses an elastic property such that it exhibits at least a one hundred percent elongation without breaking when stretched at room temperature, and will tend to return to substantially or close to its unstretched length when released. Useful thermoplastics include extrudable or moldable solid polymers, in many forms such as pellets, powders or such materials dissolved in a solvent for dipping or casting.

As used herein, the term "allylic monomer" is intended to designate a cross-linking moiety that is monomeric and contains an allyl group.

As used herein, the term "acrylic monomer or methacrylic monomer" is intended to designate a cross-linking moiety that is monomeric and contains an acrylic or methacrylic group.

Crosslinking monomers generally have more than one functional group per molecule. For example, trimethylolpropane trimethacrylate, contains three active methacrylate functional groups within each molecule. Two, three and four functional groups per molecule are common.

A monomer with only one functional group is generally not used as a crosslinker.

Particularly useful reactive monomers include, for example, triallyisocyanurate (also referred to herein as "TAIC"), triallylcyanurate (also referred to herein as "TAC"), diallyl phthalate (also referred to herein as "DAP"), and meta-phenylene dimaleimide (also referred to herein as MPDM), and combinations thereof. The TAIC is commercially available as a liquid dispersion, and, alternatively, on a silicate substrate (75% TAIC on 25% silicate) as SYNPRO PLC-4185, a product of Synpron. Other useful reactive monomers include methacrylate-containing monomers, such as trimethyolpropane trimethacrylate (TMPTMA), commercially available as Sartomer's SR-350, and acrylate-containing monomers such as trimethyolpropane triacrylate (TMPTA), commercially available as Sartomer's SR-351.

Other examples of allylic monomers include compounds such as diallyl phthalate (DAP), diallyl isophthalate, diallyl adipate, diallyl glycolate, diallyl maleate, diallyl sebacate, triallyl phosphate, triallyl aconitate, allyl trimellitate and allyl pyromellitate; diallyl carbonate; diallyl succinate; diallyl tetrabromophthalate; diethyl diallylmalonate; dimethyl diallylmalonate; and 2,2,6,6-tetrabromobisphenol A diallyl ether. 2,5-diallyl-4,5dimethyl-2-cyclopenten-1-one; diallyl fumarate; diallyl itaconate; 1,3,5-triallyl-2methoxybenzene; triallyl trimesate; triallyl trimellitate; pentaerythritol triallyl ether; tetraallyl cis, cis, cis, cis-cyclopentane-1,2,3,4-tetracarboxylate; N, N, N', N'-tetraallylethylenediamine. 1,3,5 triethyl benzene; 1,2,4 triethyl benzene; and 1,3,5 triisopropyl benzene diallyl phthalate and meta-phenylene dimaleimide; allyl methacrylate; diallyl maleate; diallyl itaconate; diallyl diglycolate; diallyl oxalate; diallyl azelate; diallyl malonate; diallyl glutarate; triallylisocyanurate; triallylcyanurate.

Other examples of acrylic or methacrylic monomers include compounds such as 1,6-hexanediol diacrylate (HDDA), 1,6-hexanediol dimethacrylate (HDDMA), neopentyl glycol diacrylate, neopentyl glycol dimethacrylate, ethylene glycol diacrylate (EGDA), ethylene glycol dimethacrylate (EGDMA), polyethylene glycol diacrylate (PEGA), polyethylene glycol dimethacrylate (PEGMA), polypropylene diacrylate, polypropylene glycol dimethacrylate, butylene glycol diacrylate, butylene glycol dimethacrylate, pentaerythritol diacrylate, 1,4-butanediol diacrylate, trimethylolpropane triacrylate, trimethylolpropane trimethacrylate, pentaerythritol triacrylate, dipentaerythritol hexaacrylate, tetramethylolmethane tetraacrylate and N,N,N',N'-tetrakis(.beta.-hydroxyethyl)ethylene-diamine acrylate. 1,6-hexane diol diacrylate (HDODA), 1,6-hexane diol dimethacrylate (HDODM), trimethylolpropane triacrylate (TMPTA), trimethylolpropane trimethacrylate (TMPTM), pentaerythritol tetracrylate (PTA), and pentaerythritol tetramethacrylate (PTM). Other useful acrylates and methacrylates include pentaerythritol triacrylate, dipentaerythritol monohydroxy penta/acrylate, 1,3-butylene glycol diacrylate, 1,4-butene diol diacrylate, 2,2-dimethyl propane 1,3-diacrylate (neopentyl glycol diacrylate), diethylene glycol diacrylate, 1,3-butylene glycol dimethacrylate, ethylene glycol dimethacrylate, diethylene glycol dimethacrylate, treithylene glycol dimethacrylate, tetraethylene glycol dimethacrylate, polyethylene glycol dimethacrylate, and ethoxylated bisphenol A dimethacrylate. ethylene glycol diacrylate, ethylene glycol dimethacrylate, diethylene glycol diacrylate, diethylene glycol dimethacrylate, 1,3- and 1,4-butane diol diacrylate, 1,3- and 1,4-butane diol dimethacrylate, tolylene-2,4-diisocyanate, 4,4'-methylene bis(phenyl isocyanate), glyceryl triacrylate, and pentaerythritol tetraacrylate. methyl methacrylate, ethyl acrylate, 2-ethylhexyl acrylate, chlorohexyl acrylate, styrene, 2-chlorostyrene, 2,4-dichlorostyrene, acraylic acid, acrylamide, acrylonitrile, t-butyl acrylate, methylacrylate, butyl acrylate, 2-(N-butylcarbamyl) ethyl methacrylate, 2-(N-ethylcarbamyl)ethyl methacrylate, 1,4-butylene dimethacrylate, or diacrylate, ethylene dimethacrylate, hexamethylene diacrylate or dimethacrylate hexamethylene diacrylate or dimethacrylate, glyceryl diacrylate or dimethacrylate, glyceryl triacrylate or trimethacrylate, pentaerythritol triacrylate or trimethacrylate, pentaerythritol tetraacrylate or tetramethacrylate, diallyl phthalate, dipentaerythritol pentaacrylate, neopentylglycol diacrylate, and 1,3,5-tri(2-methacryloyloxyethyl)-s-triazine. In order to protect the acrylates or methacrylates, antioxidants may be added.

The following acrylic monomers or methacrylate monomers are commercially available from The Sartomer Corporation, 502 Thomas Jones Way Exton, Pa. 19341. Included in the list are the chemical name followed by the Sartomer catalog number.

1,3-butylene glycol diacrylate-SR-212, 1,3-butylene glycol dimethacrylate-SR-297; 1,4-butanediol diacrylate-SR-213; 1,4-butanediol dimethacrylate-SR-214; 1,6 hexanediol diacrylate-SR-238; 1,6 hexanediol dimethacrylate-SR-239; 1-hydroxy-cyclohexyl-phenyl-ketone-Esacure KS300; 2(2-ethoxyethoxy) ethyl acrylate-SR-256; 2-hydroxyethylethylene urea-SR-512; 2-hydroxyethylethylene urea (with water)-SR-511; 2-phenoxyethyl acrylate-SR-339; 2-phenoxyethyl methacrylate-SR-340; acrylate functional monomer-PC-300; acrylated polyester oligomer-CN293; aliphatic allyl oligomer-CN9101; aliphatic diacrylate monomer-PC201; aliphatic dimethacrylate monomer-PC101; aliphatic urethane acrylate-CN2900; aliphatic urethane acrylate-CN9788; aliphatic urethane acrylate-CN9893; aliphatic urethane diacrylate oligomer with acrylate monomer diluent-CN959; alkoxylated aliphatic diacrylate-SR-9209; alkoxylated cyclohexane dimethanol diacrylate-CD-580; alkoxylated cyclohexane dimethanol diacrylate-CD-581; alkoxylated cyclohexane dimethanol diacrylate-CD-582; alkoxylated diacrylate-CD-802; alkoxylated hexanediol diacrylate-CD-560; alkoxylated hexanediol diacrylate-CD-561; alkoxylated hexanediol diacrylate-CD-564; alkoxylated lauryl acrylate-CD9075; alkoxylated neopentyl glycol diacrylate-CD9043; alkoxylated nonylphenol acrylate-SR614; alkoxylated phenol acrylate-CD9087; alkoxylated tetrahydrofurfuryl acrylate-CD-611; alkoxylated trifunctional acrylate ester-SR-9008; allyl methacrylate-SR-201; amine modified polyether acrylate oligomer-CN-501; amine modified polyether acrylate oligomer-CN-550; amine modified polyether acrylate oligomer-CN-551; amine-modified epoxy acrylate-CN2100; aromatic urethane acrylate-CN2901; benzil dimethyl ketal-Esacure KB1 benzophenone-BP; caprolactone acrylate-SR-495; chlorinated polyester acrylate oligomer-CN2201; dibutoxyethoxyethyl formal-SR-660; cycloaliphatic diepoxide-SarCat® K126; cyclohexane dimethanol diacrylate-CD-406; cyclohexane dimethanol dimethacrylate-CD-401; diethylene glycol diacrylate-SR-230; diethylene glycol dimethacrylate-SR-231; dipentaerythritol pentaacrylate-SR-399; dipropylene glycol diacrylate-SR-508; di-trimethylolpropane tetraacrylate-SR-355; epoxidized soy bean oil acrylate-CN-111; epoxy acrylate-CN-104; epoxy methacrylate-CN-151; epoxy novolak acrylate blended with sr-351-CN-112C60; ethoxylated (10) bisphenol a diacrylate-SR-602; ethoxylated (10) hydroxyethyl methacrylate-CD-572; ethoxylated (15) trimethylolpropane triacrylate-CD-9035; ethoxylated (2) bisphenol a dimethacrylate-SR-348; ethoxylated (2) hydroxyethyl methacrylate-CD-570; ethoxylated (3) bisphenol a diacrylate-SR-349; ethoxylated (3) trimethylolpropane triacrylate-SR-454; ethoxylated (3) trimethylolpropane triacrylate-SR-454HP; ethoxylated (30) bisphenol a diacrylate-CD-9038; ethoxylated (30) bisphenol a dimethacrylate-SR-9036; ethoxylated (4) bisphenol a diacrylate-SR-601; ethoxylated (4) bisphenol a dimethacrylate-CD-540; ethoxylated (4) nonyl phenol acrylate-SR-504; ethoxylated (4) nonyl phenol methacrylate-CD-612; ethoxylated (4) pentaerythritol tetraacrylate-SR-494; ethoxylated (5) hydroxyethyl methacrylate-CD-571; ethoxylated (6) trimethylolpropane triacrylate-SR-499; ethoxylated (8) bisphenol a dimethacrylate-CD-542; ethoxylated (9) trimethylolpropane triacrylate-SR-502; ethoxylated(10) bisphenol dimethacrylate-SR-480; ethoxylated(20) trimethylolpropane triacrylate-SR-415; ethoxylated(6) bisphenol a dimethacrylate-SR541;

ethyl 4-(dimethylamino) benzoate-Esacure EDB; ethylene glycol dimethacrylate-SR-206; glycidyl methacrylate-SR-379; isobornyl acrylate-SR-506; isobornyl methacrylate-SR-423; isodecyl acrylate-SR-395; isodecyl methacrylate-SR-242; isooctyl acrylate-SR-440; isopropyl thioxanthone-Esacure ITX; lauryl acrylate-SR-335; lauryl methacrylate-SR-313; metallic diacrylate-SR-636; metallic diacrylate-SR-638; metallic diacrylate-SR-705; metallic diacrylate-SR-9016; metallic dimethacrylate-SR-708; metallic monomethacrylate-SR-709; methacrylate functional monomer-PC-301; methacrylate functional monomer-PC304; methoxy polyethylene glycol (350) monomethacrylate-CD-550; methoxy polyethylene glycol (550) monomethacrylate-CD-552; neopentyl glycol diacrylate-SR-247; neopentyl glycol dimethacrylate-SR-248; octyldecyl acrylate-CD-484; oligo (2-hydroxy-2 methyl-1-4 (1-methylvinyl) phenyl propanone (emulsion)-Esacure KIP/EM; oligo (2-hydroxy-2-methyl-1-4 (1-methylvinyl) phenyl propanone and 2-hydroxy-2-methyl-1-phenyl-1-propanone (monomeric)-Esacure KIP100F; oligo (2-hydroxy-2-methyl-1-4 (1-methylvinyl) phenyl propanone and 2-hydroxy-2-methyl-1-phenyl-1-propanone (polymeric)-Esacure KIP150; pentaacrylate ester-SR-9041; pentaerythritol tetraacrylate-SR-295; pentaerythritol triacrylate-SR-444; polybutadiene dimethacrylate-CN-301; polybutadiene dimethacrylate-CN-303; polybutadiene urethane diacrylate-CN-302; polyester acrylate-CN-292; polyester acrylate oligomer-CN2200; polyester acrylate oligomer-CN2250; polyester acrylate oligomer-CN2251; polyester acrylate oligomer-CN2252; polyester acrylate oligomer-CN2253; polyester acrylate oligomer-CN2254; polyethylene glycol (200) diacrylate-SR-259; polyethylene glycol (400) diacrylate-SR-344; polyethylene glycol (400) dimethacrylate-SR-603; polyethylene glycol (600) diacrylate-SR-610; polyethylene glycol (600) dimethacrylate-SR-252; polyethylene glycol dimethacrylate-SR-210; polypropylene glycol monomethacrylate-SR-604; propoxylated (2) allyl methacrylate-CD-513; propoxylated (2) neopentyl glycol diacrylate-SR-9003; propoxylated (3) glyceryl triacrylate-SR-9020; propoxylated (3) glyceryl triacrylate-SR-9020HP; propoxylated (3) trimethylolpropane triacrylate-SR-492; propoxylated (6) trimethylolpropane triacrylate-CD-501; siliconized urethane acrylate oligomer-CN-990; stearyl acrylate-SR-257; stearyl methacrylate-SR-324; tetraethylene glycol diacrylate-SR-268; tetraethylene glycol dimethacrylate-SR-209; tetrahydrofurfuryl acrylate-SR-285; tetrahydrofurfuryl methacrylate-SR-203; triaryl sulfonium hexafluorophosphate (50% in propylene carbonate)-SarCat® KI85; tridecyl acrylate-SR489D; tridecyl methacrylate-SR493D; triethylene glycol diacrylate-SR-272; triethylene glycol dimethacrylate-SR-205; triethylene gylcol diacetate-SR-322; trifunctional acid ester-CD-9051; trifunctional acid ester-CD-9052; trifunctional acrylate ester-SR-9012; trifunctional methacrylate ester-SR-9009; trifunctional methacrylate ester-SR-9011; trifunctional urethane acrylate-CN-929; trifunctional urethane acrylate blended with sr-238-CN-945B85; trifunctional urethane acrylate blended with sr-306-CN-945A60; trimethylbenzophenone and methylbenzophenone-Esacure TZT; trimethylolpropane triacrylate-SR-351; trimethylolpropane triacrylate-SR-351HP; trimethylolpropane trimethacrylate-SR-350; tripropylene glycol diacrylate-SR-306; tripropylene glycol diacrylate-SR-306HP; tris (2-hydroxy ethyl) isocyanurate triacrylate-SR-368; tris (2-hydroxy ethyl) isocyanurate triacrylate-SR-368D; urethane acrylate-CN-962; urethane methacrylate-CN-1963; dibutoxyethoxyethyl adipate-SR-650.

When the selected polymer is a polyurethane, the reactive monomer is suitably admixed with the polyurethane-forming composition prior to preparation of the TPU, or admixed with the TPU prior to preparation of the desired thermoset polyurethane product.

Although not wishing to be bound by any particular theory, it is believed that the essentially discoloration-free appearance of certain thermoset polyurethanes produced in accordance with the present invention is attributable to the use of an aliphatic polyisocyanate in the polyurethane-forming compositions employed in the present invention. The present inventor has found that the irradiation employed in the present invention does not significantly discolor the aliphatic polyisocyanate-based polyurethane compositions employed in this invention. In contrast, such irradiation appears to discolor comparison polyurethane compositions based upon aromatic polyisocyanates.

Thermoplastic polyurethanes may comprise aliphatic or aromatic isocyanate groups in combination with aliphatic or aromatic polyester, polyether, polycarbonate, or polyurea groups. Suitable thermoplastic polyurethanes include polyester or polyether based aromatic polyurethanes such as PELLETHANE available from Dow Plastics, ESTANE available from Noveon, TEXIN available from Bayer, and TECOTHANE available from Thermedics; polycarbonate based aromatic polyurethanes such as BIONATE available from The Polymer Technology Group (PTG), and CHRONOFLEX AR available from Cardiotech; polyether based aliphatic polyurethanes such as TECOPHILIC available from Thermedics, polycarbonate based aliphatic polyurethanes such as CARBOTHANE available from Thermedics; aromatic polyurethane polyether ureas such as BIOSPAN available from PTG; polycarbonate/polyether based aromatic polyurethanes such as CARBOSIL available from PTG; or aromatic or aliphatic polyurethanes with silicone/polyether soft segments such as PURSIL available from PTG or ELASTEON available from Aortech. Other suitable polyurethane block copolymers may be used including TECOPLAST available from Thermedics, and ISOPLAST available from Dow.

Thermoplastic polyurethanes are block copolymers that are the reaction product of a diisocyante a short chain diol chain extender and a polyahl. The diisocyanate useful as a reactant in forming the polyurethanes employed in the present invention can be selected from commercially-available aliphatic or aromatic isocyanates such as, for example, 1,6-hexamethylene diisocyanate (HDI), isophorone diisocyanate (IPDI), ethylene diisocyanate, 1,4-tetramethylene diisocyanate, 2,2,4-trimethyl-1,6-hexamethylene diisocyanate, 1,10-decanemethylene diisocyanate, 1,12-dodecanemethylene diisocyanate, cyclohexane-1,3-diisocyanate, cyclohexane-1,4-diisocyanate, 1-isocyanato-2-isocyanatomethyl cyclopentane, isophorone diisocyanate, bis-(4-isocyanatocyclohexyl)-methane, 1,3- and/or 1,4-bis-(isocyanatomethyl)-cyclohexane, bis-(4-isocyanato-3-methyl-cyclohexyl)-methane, 1-isocyanato-1-methyl-4(3)-isocyanatomethyl cyclohexane, 4,4'-dicyclohexylmethane diisocyanate ($H_{12}$MDI), methylene bis-(phenylisocyanate) (MDI) an 80/20 mix of 2,4-tolylene diisocyanate (80% wt.) and 2,6-tolylene diisocyanate (20% wt.) (TDI), and combinations thereof.

The "polyahl" useful as a reactant in forming the polyurethanes employed in the present invention is an active hydrogen-containing compound that is reactive with the aliphatic polyisocyanate to produce the desired polyurethane. In addition, the term polyahl is intended to encompass compounds that react to generate an active hydrogen-containing moiety such as imines. An active hydrogen group is a group which has a hydrogen atom which, because of its position in the molecule, displays activity according to the Zerewitnoff test described by Woller in the Journal of American Chemical Society, Vol. 49, page 3181 (1927). Illustrative of such active hydrogen groups are —OH, —NH—, —COOH, —SH and —CONH—. Particularly suitably polyahls include polyols, imines (such as ketimines and aldimines), oxazolidines, and combinations thereof, preferably having a weight average molecular weight of between about 100 and about 10,000, more preferably between about 100 and about 5,000, most preferably between about 200 and about 2,000.

Suitable amines are aliphatic or cycloaliphatic, primary or secondary amines. Preferred amines are poly(alkyleneoxy) alkylamines.

Suitable polyols include polyether polyols and polyester polyols. The preferred polyols useful in the present invention have a hydroxyl functionality of no greater than about 2, more preferably less than 1.5, advantageously about 1. The polyether polyols are prepared by polymerization of alkylene oxides with water, polyhydric alcohols with two to eight hydroxyl groups, or amines. Polyester polyols are suitably prepared by a condensation reaction of a polycarboxylic acid with a polyhydric alcohol.

Some commercially available polyols include polybutadiene glycol (PBDG), poly(1,2-oxypropylene) glycol (PPG), poly(oxytetramethylene)glycol (PTMEG), poly(hexamethylene carbonate) glycol (PHC), poly(e-caprolactone) glycol (PCL), and poly(tetramethyelene adipate) glycol (PTAd).

Some commercial short chain diol chain extenders include 1,4 butanediol, 1,4-cyclohexanedimethanol, 1,4-bis(2-hydroxyethoxy)benzene, 4,4'-methylene-bis(2-chloroaniline), and trimethylene gylcol di (p-aminobenzoate).

In preparing the polyurethanes useful in the present invention, the ratio of NCO equivalents in the polyisocyanate to the OH equivalents in the active hydrogen-containing compound is balanced to yield a linear macromolecule.

Catalysts are typically employed in the polyurethane-forming reaction. Useful catalysts include those that facilitate the reaction of the polyahl with the aliphatic polyisocyanate reactants. Suitable catalysts are the organotin catalysts, alone or in combination with amine catalysts, particularly tertiary amine catalysts. Illustrative organotin catalysts include dibutyltin dilaurate, stannous octoate, and combinations thereof. Illustrative amine catalysts include the following: N,N'-dimethylethanolamine, N,N-dimethylamino-ethoxyethanol, N,N'-dimethylaminoethyl-N-methylethanolamine, N,N-dimethyl-N',N'-2-hydroxypropyl-1,3-propylene diamine, N,N,N'-trimethyl-N'-hydroxyethyl-bis(amino ethyl) ether, N,N-bis(3-dimethylaminopropyl) amino-2-propanol, and combinations thereof. The catalysts are suitably employed in the polyurethane-forming formulation in a total amount of between about 0.01% and about 5%, preferably between about 0.01% and about 1%, by weight based upon the weight of the polyurethane-forming composition.

In preparing the desired polyurethane, the polyether polyol(s), polyisocyanate(s), chain extender(s) such as polyether or polyester glycol chain extenders, and other desired components are reacted, typically at an elevated temperature. An alternative method involves batch processing, followed by grinding and extrusion of the formed elastomer as is well-known in the art. Two basic commercial methods are utilized for polyurethane polymerization. Either the pre-polymer method (2 step) or the one-shot (1 step) method although the one-shot method seems to be preferred by industry. The one-shot process, or the pre-polymer process may be carried out using either bulk polymerization or solution polymerization. In the pre-polymer method, step 1 is where the diisocyanate reacts with the polyahl to form a relatively low molecular weight pre-polymer. Then in step 2 the pre-polymer reacts with the chain extender to form the high molecular weight polyurethane elastomer. That is, in the pre-polymer process, all or a portion of one or more of the isocyanate reactive materials is reacted with a stoichiometric excess of the polyisocyanate to form an isocyanate-terminated pre-polymer. This pre-polymer is then allowed to react with the remaining isocyanate-reactive materials to prepare the polyurethane and/or polyurea elastomer. The pre-polymer can be prepared with either the polyether or the chain extender, or a mixture of both.

In the one shot method all the polyurethane components are mixed together in the proper stoichiometric balance at one time, that is, all the isocyanate-reactive components are reacted simultaneously with the polyisocyanate. In such process, it is normal practice to blend all components except the polyisocyanate into a "B-side" mixture, which is then reacted with the polyisocyanate to form the polyurethane and/or polyurea elastomer. However, the order of mixing is not critical as long as the components do not undesirably react before all components are present. The reaction mixture is then suitably placed in a mold, or extruded through continuous processing utilizing an extruder, as illustrated by the disclosures of U.S. Pat. No. 3,642,964, incorporated herein by reference in its entirety, and cured at a suitable temperature. The apparatus used for blending and molding is not especially critical. Hand mixing, conventional machine mixing, and the so-called reaction injection molding (RIM) equipment are all suitable. The polymerization proceeds to completion yielding a high molecular weight thermoplastic polyurethane elastomer with alternating hard and soft segments. The one-shot method is intended to also include the process whereby the diisocyanate has been converted to a quasi pre-polymer by reaction with a minor amount (i.e., less than about 10 percent on an equivalent basis) of polyol prior to carrying out the polyurethane forming reaction.

In preparing the desired polyurethane, urethane-forming catalysts can be used, as discussed above, as well as the usual compounding ingredients such as antioxidants or other anti-degradents. Typical antioxidants include hindered phenols, butylated hydroxytoluene ("BHT"), and the like. Other optional compounding ingredients include, for example, plasticizers, adhesion promoters, fillers and pigments like clay, silica, fumed silica, carbon black, talc, phthalocyanine blue or green, $TiO_2$, U-V absorbers, $MgCO_3$, $CaCO_3$ and the like. The compounding ingredients are suitably employed in an amount of between 0 and about 75 weight percent based upon the weight of the elastomer. When solution polymerization is used, polar solvents such as tetrahydrofuran ("THF"), dimethylformamide ("DMF"), and dimethylacetamide ("DMAC") are typically utilized.

The mixing of the reactants can be carried out at ambient temperature (typically from 20 deg C. to 25 deg C.) and the resulting mixture is then heated to a temperature of the order of about 40 deg C. to about 130 deg C., preferably to a temperature of about 90 deg C. to about 120 deg C. Alternatively, and preferably, one or more of the reactants is pre-heated to a temperature within the above ranges before the admixing is carried out. Advantageously, in a batch procedure, the heated reaction components are subjected to degassing in order to remove entrained bubbles of air, water, or other gases before the reaction takes place. This degassing is accomplished conveniently by reducing the pressure under which the components are maintained until no further evolution of bubbles occurs. The degassed reaction components are then admixed and transferred to suitable molds or extrusion equipment or the like and cured at a temperature of the order of about 20 deg C. to about 115 deg C. The time required for curing will vary the temperature of curing and also with the nature of the particular composition, as is known in the art.

Polyamide/polyether block (PEBA) copolymers preferably have polyamide and polyether blocks or segments linked through ester linkages, i.e. polyamide/polyether polyesters. Polyamide/polyether polyester PEBA block copolymers are made by a molten state polycondensation reaction of a dicarboxylic polyamide and a polyether diol. The result is a short chain polyester made up of blocks or segments of polyamide and polyether. Such polymers are made up of at least two polyamide and at least two polyether segments. The polyamide and polyether blocks are not miscible. Thus, the materials are characterized by a two-phase structure having a thermoplastic region that is primarily polyamide and an elastomer region that is rich in polyether. The polyamide segments are semi-crystalline at room temperature. The generalized chemical formula for these polyamide/polyether polyester block copolymers may be represented by the following formula:

$$HO-(CO-PA-CO-PE-O)_n-H$$

in which CO is a C=O moiety, PA is a polyamide hard segment, PE is a polyether soft segment, and the repeating number n is between 5 and 10. The polyamide hard segment is a polyamide of $C_6$ or higher, preferably $C_{10}$-$C_{12}$, carboxylic acids; $C_6$ or higher, preferably C10-C12, organic diamines; or C6 or higher, preferably C10-C12, aliphatic omega.-amino-alpha.-acids. The percentage by weight of the block copolymer attributable to the polyamide hard segments is between about 50% to about 95%. The polyether soft segment is a polyether of C2-C10 diols, preferably C4-C6 diols.

The polyamide segments are suitably aliphatic polyamides, such as nylons 12, 11, 9, 6, 6/12, 6/11, 6/9, or 6/6. Most preferably they are nylon 12 segments. The polyamide segments may also be based on aromatic polyamides but in such case significantly lower compliance characteristics are to be expected. The polyamide segments are relatively low molecular weight, generally within the range of 500-8,000, more preferably 2,000-6,000, most preferably about 3,000-5,000. Another range that is of interest is 300-15,000.

The polyether segments are aliphatic polyethers having at least 2 and no more than 10 linear saturated aliphatic carbon atoms between ether linkages. More preferably the ether segments have 4-6 carbons between ether linkages, and most preferably they are poly(tetramethylene ether) segments. The repeating unit of poly(tetramethylene ether) is $-[(CH_2)_4-O-]_n$. Examples of other polyethers that may be employed in place of the preferred tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, preferably between 650 and 1,000. Another range that is of interest is 200-6,000.

The weight ratio of polyamide to polyether in the polyamide/polyether polyesters used in the invention desirably should be in the range of 50/50 to 95/5, preferably between 60/30 and 92/08, more preferably, between 70/30 and 90/10.

Polyamide/polyether polyesters are sold commercially under the PEBAX trademark by Atochem North America, Inc., Philadelphia, Pa. A suitable polymer grade for the intravascular balloon catheter of the invention is the PEBAX® 33 series. The PEBAX® 33 series is believed to comprise polyamide 12 (also known as Nylon 12 or PA 12) hard segments and polytetramethylene ether soft segments. In the embodiment as a balloon, 100% PEBAX or a blend of PEBAX and a polyamide, preferably PEBAX and nylon, especially nylon 11 or 12, can be utilized in the present invention. In an embodiment in which the balloon is a co-extruded multi-layered balloon, at least one layer can be formed of PEBAX.

The PEBAX 7033 and 6333 polymers are made up of nylon 12 segments and polytetramethylene ether segments in about 90/10 and about 80/20 weight ratios, respectively. The average molecular weight of the individual segments of nylon 12 is in the range of about 3,000-5,000 grams/mole and of the polytetramethylene ether segments are in ranges of about 750-1,250 for the 6333 polymer and about 500-800 for the 7033 polymer. The intrinsic viscosities of these polymers are in the range of 1.33 to 1.50 dl/g.

While the PEBAX-type polyamide/polyether polyesters are most preferred, it is also possible to use other polyamide elastomer polymers with the physical properties specified herein and obtain similar compliance characteristics as Pebax. Such other polyamide elastomer polymers generally have polyamide segments and elastomer segments. The polyamide segments can be any aromatic or aliphatic polyamide and the elastomer segment can be any polyether, polyester or combination thereof. For example, Vestamid E, (Degussa Corporation) is a PA 12 elastomer, PEBA type polymer which comprises polylaurinlactam (also known as PA12, nylon 12 or polyamid 12) hard segments and polytetrahydrofuran soft segments. The repeating unit of polytetrahydrofuran is (CH.sub.2).sub.4-O.sub.n which is the same repeat segment as polytetramethylene ether. Polytetrahydrofuran is therefore another name for polytetramethylene ether. Therefore, Vestamide E PEBA polymer series is similar to the Pebax 33 series of PEBA polymers commercially marketed by Atochem. They may differ in the molecular weight and proportion of the hard and soft segments, and their method of manufacture may also differ in detail. However, chemically they are the same. Another PEBA polymer, Grilamid (EMS-Chemie), is less desireable than the Pebax or Vestamid E polymers because it contains amide linkages between the hard and soft segment rather than the ester linkages characteristic of Pebax and Vestamid E.

It is also possible to utilize polyester/polyether segmented or randomized block copolymers also known as polyester elastomer block copolymers in this invention. Such polymers are made up of at least two polyester and at least two polyether segments. The polyether segments are the same as previously described for the polyamide/polyether block copolymers useful in the invention. The polyester segments are polyesters of an aromatic dicarboxylic acid and a two to four carbon diol. The generalized formula is $$[-(CH2)_n-O]_x[(CH2)_m-O-CO-PH-COO-]_y$$

where CO signifies a C=O moiety, COO signifies a carboxylic moiety, and PH signifies a phenyl moiety, and n can be between 2 and 10 and m can be 2 or 4

Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids.

Polyester/polyether block copolymers are poly(butylene terephthalate)-block-poly(tetramethylene oxide) polymers such as Arnitel EM 740, sold by DSM Engineering Plastics or Hytrel polymers, sold by DuPont.

Also useful in the present invention are the polyamides which can be the product of the polycondensation of dicarboxylic acids and diamines, or the polycondensation of omega-aminoacids, or the ring opening and polymerization or polyaddition of cyclic amides (e.g. caprolactam). These polyamides can be homopolymers or copolymers and can be aliphatic and/or aromatic (sometimes called polyaramides) and are genericaly referred to as "Nylon". Examples of homopolymers are Nylon 6, Nylon 11 and Nylon 12. Examples of copolymers are Nylon 6,6, Nylon 6,9 and Nylon 6,12. Of particular usefulness are the the Nylon 11 and Nylon 12 polyamides marketed by Atochem under the Rilsan trademark.

The polymers produced in accordance with the present invention are useful in a variety of applications, including sealants, elastomers, coatings, adhesives, and in the fabrication of a wide variety of household, commercial, and industrial products. For example, the present invention is suitably employed to produce crosslinked polymers that are useful in producing medical catheters and angioplasty balloons. As another illustration, the present invention is suitably employed to produce flexible wire and cable jackets having improved temperature and fluid resistance, as compared analogous products made from thermoplastic materials. Other illustrative uses for the thermoset polymers produced in accordance with the present invention include the following: orthodontic ligatures which last longer than those made from prior art TPU's; seals, gaskets and o-rings which are easier to fabricate than those made from prior art cast polyurethanes and exhibiting better temperature stability, compression set and fluid resistance than those made from prior art TPU's; sneaker and shoe soles that are longer wearing than those made from prior art TPU's; longer lasting toner wiper blades for copiers and laser printers, as compared to those made from prior art TPU's; heat shrink tubing; and devices and particularly medical devices consisting entirely or partly of the crosslinked polymers of the present invention, and insulated or jacketed wires which last longer inside body parts and cavities than those made from thermoplastic materials.

For example a medical device could be encapsulated by the crosslinked polymer of the present invention by preparing a shaped object comprising a crosslinked polymer of the present invention, said shaped object would be expanded to a larger size than the medical device to be encapsulated, by a heating and forming process, and then cooled to retain the expanded size. Said expanded object would possess the characteristic of "memory" due to the crosslinked polymer comprising the object. The device or medical device to be encapsulated would be placed within the expanded shaped object with "memory", and heat applied to cause the expanded shaped object to contract and encapsulated the device within.

Another application of the present invention relates to sterilization of medical devices or products and other products such as food related products, and the use of radiation to sterilize medical devices or products or other devices or products. Several sterilization methods are employed in the medical and other industries, these include steam sterilization, sterilization with etylene oxide gas, and sterilization by exposure to gamma, x-ray or electron beam radiation. When the object to be sterilized contains one or several polymers, the possible degradation, deformation, discoloration, softening, embrittlement or other undesireable change in of one or more of the polymers in the object can be an issue. For example, beta radiation, such as from an electron beam, or gamma radiation, such as from a cobalt-60 source, is often used to sterilize medical devices, equipment or products. This is a particularly convenient means of sterilization since the items may be packed in bulk, or in individually sealed clean packages, and irradiated after packaging. Such treatments yield sterile instruments and devices without the need for special handling or repackaging after sterilization. Thus, sterility and enhanced patient safety are assured. However, because certain polymers tend to degrade when exposed to sterilizing levels of radiation, such treatment may be inappropriate for medical devices incorporating those degrading polymer components. By incorporating a monomer crosslinker into a polymer in accordance with this invention, the properties of a polymer can often be improved or stabilized and degradation by the effects sterilizing is mitigated.

Therefore by adding a monomer crosslinker to a polymer, the present invention can be utilized to stabilize polymers for the purpose of mitigating any degradation which might occur from the application of sterilizing processes and therefore enable a sterilization and/or radiation tolerant polymer, article, product, or device.

Polyurethanes, polyamide elastomers, nylons, and polyester elastomers are excellent materials for use in a variety of applications, particularly medical and food packaging applications. However certain limitations within these materials becomes evident when exposed to a sterilization process. For example, polyurethane materials tend to soften and deform when sterilized at high temperature by steam or turn yellow or some other color, and/or lose some of their physical properties when treated with high energy radiation, particularly beta and gamma radiation. In addition, polyamide elastomers tend to embrittle or otherwise degrade when radiation sterilized. We have discovered that the tolerance to radiation and heat of these crosslinking monomer containing polymers and others for use in a sterilization process can be enhanced relative to a polymer which does not contain the monomer crosslinker.

For example, by incorporation of the monomer crosslinker into the polymer and then crosslinking it with radiation as per this invention, the crosslinked polymer exhibits higher heat stability and therefore shows greater tolerance to the conditions encountered in steam sterilizers. This tolerance is evidenced by decreased deformation, and decrease physical property degredation including a reduction in surface tackiness.

Without being bound by any specific theory we believe that this is because the predominant response of the polymer to radiation, in the presence of the monomer crosslinker, is crosslinking. Crosslinking results in an inprovement in physical properties. In the absence of the monomer crosslinker the predominant response of the polymer is chain scission. Chain scission results in a degradation in physical properties.

In another example, by incorporation of a monomer crosslinker into a polymer, forming it into an object, and crosslinking it with radiation as per this invention, the crosslinked object can exhibit higher stability and less degradative physical property changes when exposed to subsequent radiation doses as might be employed in a sterilization procedure-relative to the same object which is uncrosslinked.

Also, by incorporation of a monomer crosslinker into a polymer, forming it into an object, the un-crosslinked object can exhibit higher stability and less degradative physical property changes when exposed to subsequent radiation doses than the same object lacking the monomer crosslinker when exposed to a radiation sterilization procedure.

Radiation is often used to modify the surface or to graft a material to the surface of a polymer. The degrading of the underlying polymer substrate by the radiation used to effect the surface modification or grafting can be an issue. In an manner similar to the sterilization application, by adding a monomer crosslinker to a polymer, the present invention can be utilized to stabilize a polymer substrate for the purpose of mitigating any degradation which might occur to the substrate from the application of radiation to surface modify or graft a substance to that substrate.

The term "radiation tolerant" and "sterilization tolerant" generally means a resistancy to deterioration in mechanical properties, color or other properties experienced by certain materials, when subjected to radiation or a sterilization process. These processes can include steam sterilization, and radiation sterilization. The acceptable level of radiation or sterilization tolerance depends, at least in part, upon the application or end-use of the irradiated or sterilized material. For example, in applications requiring very stiff, clear, and visually appealing articles, a smaller deterioration in properties may render the article useless, while other applications might be more forgiving.

Useful applications articles or devices which would benefit from increased radiation or sterilization tolerance include, food packaging material comprising film and a self-supporting multilayered structure which includes simple wrapping film, film useful for bubble or blister packing, and the materials useful for producing the containers known as "liquid-boxes" as well as other useful pouches, bottles or hybrid-type containers. The useful food packaging materials may be formed by extrusion, blowing, lamination, or combinations thereof.

Further useful applications articles or devices which would benefit from increased radiation or sterilization tolerance include medical devices which are suitable for 1) intravenous (IV) use, 2) transport, storage, dispensing, or combinations thereof of medications, 3) surgical use, 4) medical examination, 5) culture growth, preparation, examination, or combinations thereof, 6) other laboratory operations, or 7) combinations thereof.

Such medical devices include such items as 1) IV catheters, probes, or expanding device such as an arterial "balloons", or combinations thereof, 2) IV fluid container or dispenser, IV tubing, IV valve, IV injection port, unit-dose package, syringe or syringe barrel, or combinations thereof, 3) forceps, handle or holder for surgical instruments, surgical probe, curette, clamp or tying device, retractor, biopsy sampler, gowns, drapes, masks, filters, filter membranes, caps, booties, or combinations thereof, 4) speculums, probes, retractors, forceps, scrapers, samplers, or combinations thereof, 5) a culture dish, culture bottle, cuvette, smear slide, smear or sample container, or combinations thereof.

Further specific examples of useful medical devices which would benefit from increased radiation or sterilization tolerance made by this invention include disposable and reusable hypodermic syringes, particularly the barrels and plunger parts. This could include prefilled hypodermic syringes for drug packaging and delivery as well as ancillary parts of syringes including needle hubs and needle sheaths. This could also include parts for parenteral kits including valves, cannula hubs, connectors, and cannula shields. Parts for catheters are also included, particularly cannula hubs, connectors, and cannula shields. Useful labware may also be produced including test tubes, culture tubes, and centrifuge tubes as well as vacuum blood collection tubes and ancillary parts including needle adapters/holders, and shields as well as drug vials, caps, and seals. Measuring devices such as droppers, eye-droppers, pipettes, and graduated feeding tubes, cylinders, and burets may also usefully benefit from increased radiation or sterilization tolerance including infant or disabled nursers and nurser holders.

Other useful articles and goods which may benefit from increased radiation or sterilization tolerance include labware, such as roller bottles for culture growth and media bottles, instrumentation sample holders and sample windows; liquid storage containers such as bags, pouches, and bottles for storage and IV infusion of blood or solutions; packaging material including those for any medical device or drugs including unit-dose or other blister or bubble pack as well as for wrapping or containing food preserved by irradiation.

Other items benefiting from increased radiation or sterilization tolerance include medical tubing and valves for any medical device including infusion kits, catheters, and respiratory therapy, as well as packaging materials for medical devices or food which is irradiated including trays, as well as stored liquid, particularly water, milk, or juice, containers including unit servings and bulk storage containers as well as transfer means such as tubing, pipes, and such.

These devices may be made or formed by any useful forming means for forming polymers. This include, molding including compression molding, injection molding, blow molding, and transfer molding; film blowing or casting; extrusion, and thermoforming; as well as by lamination, pultrusion, protrusion, draw reduction, rotational molding, spin-bonding, melt spinning, melt blowing; or combinations thereof. Use of at least thermoforming or film applications allows for the possibility of and derivation of benefits from uniaxial or biaxial orientation of the radiation tolerant material.

The polymer employed in the present invention are suitably shaped into the desired product configuration while in the thermoplastic state, and then irradiated to convert to the thermoset product. In certain instances, as in heat shrink tubing, the thermoset product could be further formed into another shape or product by further processing. The thermoplastic polymer can be in solid form, such as pellets, prior to forming the desired polymer product. Alternatively, solid thermoplastic polymer can be dissolved in organic solvent, and used for dipping, spraying or otherwise coating the dissolved polymer onto a substrate, and then the coating is suitably thermoset by irradiation.

As used herein, the term "molecular weight" is intended to designate number average molecular weight. All percents used herein are percents by weight unless otherwise specified. As used herein, the term "phr" denotes "parts by weight per hundred parts of resin".

The following Examples are intended to illustrate, but in no way limit the scope of, the present invention.

EXAMPLE 1

Part A—Preparation and Testing of a Thermoset Polyurethane of the Present Invention A sample of dried aliphatic polyester, thermoplastic polyurethane resin, having a hardness of 80 Shore A and a melt index of 2 at 165 deg C., was compounded with 4 phr of SYNPRO PLC-4185 (75% TAIC on 25% silicate) allylic monomer to yield a mixture containing 3 phr TAIC. This mixture was compression molded at 125 deg C. for 10 minutes to yield a 6"×6"×0.070" plaque. The plaque was exposed to 14 Mega Rads of high energy electron beam irradiation in order to convert the plaque to a thermoset plaque.

After irradiation the thermoset plaque was tested for various physical properties in accordance with ASTM tests as identified in Table 1 below. The test results are provided in Table 1.

TABLE 1

| Physical Properties | 14 MRads |
|---|---|
| Ultimate elongation at break (%) | 425 |
| 200% Modulus (psi) | 900 |
| Compression set (%) | 58.5 (72 hours at 100 deg C.) |
| Color change (visual) | minimal |

| Fluid Resistance | | 14 MRads | |
|---|---|---|---|
| Fluid | Temp | Time | Observation |
| Mil-L-16884 | 121 deg C. | 2.5 hrs | swell + 13%, brown stained, somewhat tacky |
| Tetrahydrofuran | 20 deg C. | 2.5 hrs | swelled, very friable, did not dissolve** |
| 100% IPA* | 20 deg C. | 2.5 hrs | no change |
| 50% IPA* | 20 deg C. | 2.5 hrs | no change |
| Water, distilled | 20 deg C. | 2.5 hrs | no change |

(*IPA = isopropyl alcohol)
(**unirradiated pellets completely dissolved)

Part B—Temperature Stability Test

The irradiated polyurethane of Part A above did not melt or flow at elevated temperatures as demonstrated by probing the irradiated plaque with an electrically heated solder iron tip at a temperature of approximately 300 deg C.

Part C—Comparison with Aromatic Polyisocyanate-based Polyurethanes

Dow's PELLETHANE 55D aromatic polyisocyanate-based polyurethane resin was compounded with 3 phr TAIC allylic monomer, and exposed to 15 Mrads of high energy electron beam irradiation. No crosslinking was observed based upon the results of a hot iron test (described hereinabove) on this composition, and the physical properties were unchanged relative to the unirradiated neat pellets. Instead, the irradiated material discolored by turning dark brown.

In a second experiment, Dow's PELLETHANE 55D aromatic polyisocyanate-based polyurethane resin Pellethane 55D was compounded with 3 phr of TMPTMA (an acrylic monomer) and exposed to 15 Mrads of high energy electron beam irradiation. No crosslinking was observed in the hot iron test as described above, and the physical properties were unchanged relative to the unirradiated neat pellets. The irradiated material turned dark brown.

The hot iron test is only a screening test. It is not considered a rigorous test for crosslinking. Therefore, a standard test, ASTM D 2765 (method A), using Tetrahydrofuran as the solvent, for determination of the gel content (insoluble fraction) of crosslinked platics, was employed to verify the results obtained reported above with the "hot iron" test.

The ASTM D 2765 test consists of immersing a known weight of polymer in boiling solvent heated to its boiling point for a designated time period. At the end of the the designated time period, the polymer remaining is recovered, dried and weighed. The weight of of polymer remaining divided by the original weight is designated the insoluble fraction or gel fraction or % gel (all equivalent terms). If the weight of of polymer remaining at the end of the time period is the same as the starting weight, then 100% gel is reported. If the weight of of polymer remaining at the end of the time period is half the starting weight, then 50% gel is reported. If all the polymer dissolved, then 0% gel is reported. The % gel number is considered to be a relative measure of the degree of crosslinking present in the polymer material under test. The larger the % gel number, the greater the degree of crosslinking present within the polymer. An uncrosslinked polymer will yield a 0% gel number when subjected to this test in an appropriate solvent. The polymer will be considered crosslinked if the % gel number are greater than 0%. Useful property improvements are usually noticed when the % gel number is above 25%, but this number is not absolute and varies depending on the specific type and grade of polymer species.

For Pellethane TPU, 1 gram samples of the material under test were refluxed, in a Soxhlet type apparatus using pre-weighed thimbles to hold the sample, with boiling tetrahydrofuran solvent for 48 hours. After 48 hours, the samples were withdrawn from the apparatus, dried in a vacuum oven, and weighed. An average based on 5 identical samples in 5 separate tests under identical conditions was reported as the % gel number.

The results of the gel testing is reported in table 2. below.

TABLE 2

| Polymer | (wt %) Monomer | Radiation Dose (Mrad) | % Gel |
|---|---|---|---|
| Pellethane 2363-55D | NONE | 0 | 0 |
| Pellethane 2363-55D | 3% TAIC[1] | 15 | 0 |
| Pellethane 2363-55D | 3% TMPTMA[2] | 10 | 36 |
| Pellethane 2363-55D | 3% TMPTMA | 20 | 57 |
| Pellethane 2363-55D | 6% TTEGMA[3] | 20 | 58 |
| Pellethane 2363-55D | 3% TMPTMA | 0 | 0 |
| Pellethane 2363-80A | NONE | 0 | 0 |
| Pellethane 2363-80A | 3% TMPTMA | 0 | 0 |
| Pellethane 2363-80A | 3% TMPTMA | 10 | 59 |
| Pellethane 2363-80A | 3% TMPTMA | 20 | 63 |

[1]TAIC, Triallylisocyanurate
[2]TMPTMA, Trimethylpropane trimethacrylate
[3]TTEGMA, Tetraethylene glycol dimethacrylate For the Pellethane 55D with 3 phr TAIC as the monomer crosslinker at 15 Mrad the % gel was 0. This indicates that Pellethane 55D with 3 phr TAIC as the monomer crosslinker does not crosslink at 15 Mrads of radiation, which agrees with the results obtained with the "hot iron test".

For Pellethane 55D with 3 phr TMPTMA as the monomer crosslinker and a 10 Mrad dose the % gel was 36% gel at 10 Mrads, and 57% gel at a 20 Mrads. This indicates that Pellethane 55D with 3 phr TMPTMA as the monomer crosslinker does crosslink with radiation, which conclusion does not agree with the results observed with the "hot iron test". Since the hot iron test is merely a screening test indications of crosslinking, it can not be considered definitive. Rather, as occurred with respect to initial conclusions drawn for Pellethane 55D irradiated in the presence of TMPTMA, the "hot iron" test, can be misleading. Therefore our initial conclusion that aromatic polyurethanes did not crosslink with TMPTMA was incorrect. Testing in accordance with ASTM D-2765, indicated that Pellethane 2363-55D did in fact crosslink with radiation when TMPTMA was used as the monomer crosslinker. Further experiments with other versions of of Pellethane and different crosslinking monomers confirms that Pellethane, an aromatic TPU will generally crosslink in the presence of irradiation and methacrylic and acrylic monomer crosslinkers.

Dow PELLETHANE 80A aromatic polyisocyanate-based polyether polyurethane resin of shore hardness 80A, was compounded with 3 phr TMPTMA (Sartomer SR-350—trimethylolpropane trimethacrylate, a methacrylic monomer), and exposed to 20 Mrads of high energy electron beam irradiation. Gel testing demonstrated 59% gel at 10 Mrads, and 63% gel at 20 Mrads, confirming the presence of crosslinking. Additionally, the elongation of the irradiated material decreased to 400% compared with the unirradiated material whose elongation was 450%. The irradiated material was observed to change color from a tan color to an orange color. Similar results were observed when the same material was compounded with 3 phr of TMPTA (Sartomer SR-351—trimethylolpropane triacrylate, an acrylic monomer)

In another experiment, Dow PELLETHANE 2363-55D aromatic polyisocyanate-based polyether polyurethane resin was compounded with 6 phr of TTEGDMA (Tetraethylene glycol dimethacrylate—UCB Chemicals—a methacrylic monomer) and exposed to 20 Mrads of high energy electron beam irradiation. A "Gel extraction" test was performed whereby a sample of the polymer material exposed to 20 Mrads of electron beam irradiation was boiled for 2 days in Tetrahydrofuran. At the end of the gel test, 58% of the original irradiated material remained undissolved (demonstrating crosslinking occurred), compared with 0% remaining of the unirradiated 55D Pellethane material when exposed to the same test conditions (indicative that no crosslinking occurred). The irradiated material also turned orange.

The last results contradict the findings of Keiji Ueno (U.S. Pat. No. 4,820,782), who reported "to the great surprise of the inventors, all the urethane resin compositions incorporating the polyfunctional monomers other than trimethylolpropane trimethacrylate, trimethylolpropane triacrylate, and triacrylformal deformed completely when they were subjected to a thermal deformation test at 180 degree C." That is, according to the '782 Patent of Ueno, urethane resins will crosslink only with the polyfunctional monomers trimethylolpropane trimethacrylate, trimethylolpropane triacrylate, and triacrylformal. However we demonstrate crosslinking of a urethane composition using a methacrylic monomer that Ueno states would not cause crosslinking. We conclude that aromatic TPU's will crosslink in the presence of radiation and any polyfunctional acylic or methacrylic monomer.

Similar results were demonstrated over a wide range of radiation doses, namely between 0.5 and 100 Mrads.

Part D—Comparison of Crosslinked Versus Uncrosslinked TPUs in a Weighted Probe Test A comparison was made between the physical property stability of a crosslinked polymer and that of an uncrosslinked polymer when exposed to elevated temperatures using a Thermo-Mechanical Analyzer ("TMA"). Briefly, the test regimen was conducted by placing a small piece (approximately 2 millimeters thick) of polymer is heated to an elevated temperature in the TMA, and a round glass probe weighted to 5 grams is applied to the sample. The sample was heated in the TMA to provide a controlled rate of temperature increase of 5 degrees Centigrade per minute, and the resulting probe penetration into the sample of TPU was recorded as a function of time. The test results showed that the probe caused heat deformation of the uncrosslinked TPU at a much lower temperature than that at which it caused deformation of the crosslinked TPU. By way of illustration, uncrosslinked TPU was initially penetrated by the probe at a polymer temperature of 115 degrees Centigrade. In contrast, TPU exposed to 20 MRads of radiation before being placed in the TMA resisted initial penetration until a polymer temperature of 239 degrees Centigrade was reached. These results demonstrate the improved dimensional heat stability of the crosslinked TPU as compared to the uncrosslinked TPU.

Part E—Comparison of Effect of Radiation on TPU with and without Monomer Crosslinker Pellethane 2363-80A was compounded with 3% TMPTMA (trimethylolpropane trimethacrylate), and extruded into tubing of 0.072×0.082 in (ID×OD). After application of ebeam radiation at a dose level of 10 Mrad, the elongation of the of the material containing 3% TMPTMA was observed to decrease about 11%. Whereas the elongation of a comparable sample of Pellethane 2363-80A, without TMPTMA was observed to increase 11%. An increase in elongation usually reflects a degradation in a material, while a decrease in elongation usually reflects crosslinking in a material as opposed to degredation. The test results are shown in table 3.

TABLE 3

| Pellethane 2363-80A | With TMPTMA | Without TMPTMA |
|---|---|---|
| Elongation (%) at 0 MRads | 450 | 450 |
| Elongation (%) at 10 MRads | 400 | 500 |
| % Change | −11% | +11% |

EXAMPLE 2

Physical Property Testing of Block Copolymers Before and After Irradiation

Samples of several block copolymers were prepared and tested as follows: Each polymer identified in Table 1 below was mixed with 3% (by weight) of pure liquid TAIC (triallyisocyanurate) in a twin screw extruder, and the resulting mixture was strand extruded and pelletized. The extruded product was dryed and compression molded into plaques having dimensions of 6 inches×6 inches×0.080 inches, and then irradiated with electron beam irradiation at the indicated dosage shown in Table 1 below.

Tensile bars of the extruded product were die cut and the tensile strength and elongation at break for these samples were measured. The melting ability of these samples was determined by applying a hot instrument to them. The results are displayed in Table 4 below.

TABLE 4

Change in physical properties related to radiation dose for certain modified polymers

| Material | Dose* | Color | Melts | Tb** | Eb*** |
|---|---|---|---|---|---|
| Pebax-72D | 0 | white | yes | 6460 | 190 |
| " | 10 | green | no | 6740 | 105 |
| " | 12.5 | green | no | 6770 | 95 |
| " | 15 | green | no | 6800 | 90 |
| Hytril-72D | 0 | white | yes | 4895 | 200 |
| " | 10 | white | no | 4890 | 170 |

TABLE 4-continued

Change in physical properties related to radiation dose for certain modified polymers

| Material | Dose* | Color | Melts | Tb** | Eb*** |
|---|---|---|---|---|---|
| " | 12.5 | white | no | 4180 | 20 |
| " | 15 | grey | no | 4830 | 15 |

(*Units are in MegaRads).
(**Tensile strength at break in psi).
(***Elongation at break in percent).

The results as provided in Table 3 above demonstrate that HYTREL and PEBAX block co-polymers having a Shore D hardness of 72, exhibit changes in mechanical properties consistent with crosslinking of these polymers. The HYTREL polymer is a co-polyester polymer of poly(1,4 butanediol terephthalate) and poly(alkylene ether terephthalate), whereas the PEBAX polymer is a co-poly(ether-ester-amide) polymer. Both polymers exhibit decreasing elongation with increasing radiation dose, and both no longer melt at the temperature tested, namely 325 degrees Centigrade, at high radiation doses. In addition, PEBAX polymer shows an increase in tensile strength with increased radiation dose, while the tensile strength of HYTRIL polymer is essentially unchanged with increased radiation dose.

Similar results were demonstrated with acrylic and methacrylic monomer crosslinkers for the polyester elastomers and the polyamide elastomers.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A radiation cross-linkable medical angioplasty balloon or radiation cross-linkable medical catheter made from a thermoplastic cross-linkable composition, said thermoplastic cross-linkable composition comprising: (a) a copoly(ether-ester-amide) polymer; and (b) a monomer cross-linker comprising acrylate monomer cross-linkers, said monomer cross-linker present in said composition in an amount sufficient to provide cross-linking of at least a portion of said thermoplastic polymer to convert said portion from a thermoplastic to a thermoset state upon irradiation of said composition with energy from a radiation source.

2. The radiation cross-linkable medical angioplasty balloon or radiation cross-linkable medical catheter of claim 1, wherein said thermoplastic polymer is a thermoplastic elastomer.

3. The radiation cross-linkable medical angioplasty or radiation cross-linkable medical catheter balloon of claim 1, wherein said thermoplastic polymer is a block copolymer containing hard and soft segments.

4. The radiation cross-linkable medical angioplasty balloon or radiation cross-linkable medical catheter of claim 1, wherein said monomer cross-linker is trimethylolpropane triacrylate.

5. A radiation cross-linked medical angioplasty balloon or radiation cross-linked medical catheter made by irradiating the radiation cross-linkable medical angioplasty balloon or radiation cross-linkable medical catheter of claim 1 with energy from a radiation source.

6. The radiation cross-linked medical angioplasty balloon or radiation cross-linked medical catheter of claim 5, wherein said energy is in the form of free radical initiating or ionizing radiation selected from the group consisting of beta particles, gamma particles, ultraviolet radiation, electron beam radiation, and combinations thereof.

7. A radiation cross-linked medical angioplasty balloon or radiation cross-linked medical catheter made from a cross-linked composition, wherein said cross-linked composition is produced by irradiating a cross-linkable composition comprising: (a) a copoly(ether-ester-amide) polymer; and (b) a monomer cross-linker comprising acrylate monomer cross-linkers, said monomer cross-linker present in said composition in an amount sufficient to cross-link at least a portion of said thermoplastic polymer to convert said portion from a thermoplastic to a thermoset state upon irradiation of said composition with energy from a radiation source.

8. The radiation cross-linked medical angioplasty balloon or radiation cross-linked medical catheter of claim 7, wherein said thermoplastic polymer is a thermoplastic elastomer.

9. The radiation cross-linked medical angioplasty balloon or radiation cross-linked medical catheter of claim 7, wherein said thermoplastic polymer is a block copolymer containing hard and soft segments.

10. The radiation cross-linked medical angioplasty balloon or radiation cross-linked medical catheter of claim 7, which is produced by irradiating said cross-linkable composition with energy in the form of free radical initiating or ionizing radiation selected from the group consisting of beta particles, gamma particles, ultraviolet radiation, electron beam radiation, and combinations thereof.

11. The radiation cross-linked medical angioplasty balloon or radiation cross-linked medical catheter of claim 7, wherein said monomer cross-linker is trimethylolpropane triacrylate.

12. An article suitable for sterilization, surface modification, or surface grafting, comprising
a cross-linked composition, wherein said cross-linked composition is produced by irradiating, with gamma or electron beam radiation, a cross-linkable composition comprising:
(a) a copoly(ether-ester-amide) polymer, wherein the polyamide segments of the copoly(ether-ester-amide) polymer consist of polyamide Nylon 12 segments, and
(b) a monomer cross-linker selected from the group consisting of methacrylate monomer cross-linkers, acrylate monomer cross-linkers, and combinations thereof; said monomer cross-linker present in said cross-linkable composition in an amount sufficient to cross-link at least a portion of said thermoplastic polymer to convert said portion from a thermoplastic to a thermoset state upon gamma or electron beam irradiation of said composition with energy from a gamma or electron beam radiation source,
wherein the amount of cross-linked composition is sufficient to increase the tolerance to said sterilization, surface modification or surface grafting of the cross-linked article over that of the article alone without the cross-linked composition.

13. The article of claim 12, wherein said article is a medical device.

14. The article of claim 12, wherein said article has been subjected to gamma or electron beam radiation or heat in an amount sufficient to sterilize that article or wherein said article has been subjected to gamma or electron beam radiation in an amount sufficient to graft or modify the surface of that article.

15. An wholly or partially encapsulated device, wholly or partially encapsulated with a cross-linked composition produced by irradiating a cross-linkable composition comprising: (a) a copoly(ether-ester-amide) polymer, and (b) a monomer cross-linker selected from the group consisting of allylic monomer cross-linkers, methacrylate monomer cross-linkers, acrylate monomer cross-linkers, and combinations thereof; said monomer cross-linker present in said composition in an amount sufficient to provide cross-linking of at least a portion of said thermoplastic polymer from a thermoplastic to a thermoset state upon irradiation of said composition with energy from a radiation source, and wherein the cross-linked encapsulation composition is expanded to a larger size than the device to be encapsulated, by a heating and forming process, and then cooled to retain the expanded size, said expanded cross-linked encapsulation composition possessing the characteristic of "memory" due to the cross-linked polymer comprising the cross-linked encapsulation composition, and wherein the device to be wholly or partially encapsulated is placed within the expanded shaped object with "memory", and wherein heat is applied to cause the expanded cross-linked encapsulation composition with "memory" to contract and wholly or partially encapsulate the device within.

16. The device of claim 15, wherein said device is a medical device.

17. A wholly or partially encapsulated medical device comprising:
    a medical device;
    a radiation cross-linked composition wholly or partially encapsulating said medical device and made by irradiating a radiation cross-linkable composition with energy from a radiation source, the radiation cross-linkable composition comprising:
        (a) a copoly(ether-ester-amide) polymer; and
        (b) a monomer cross-linker selected from the group consisting of allylic monomer cross-linkers, methacrylate monomer cross-linkers, acrylate monomer cross-linkers, and combinations thereof,
    wherein the radiation cross-linked composition is in the form of a heat shrunk shaped object.

18. The wholly or partially encapsulated medical device of claim 17, wherein the polyamide segments of the copoly (ether-ester-amide) polymer consist of polyamide Nylon 12 segments.

19. The wholly or partially encapsulated medical device of claim 17, wherein the monomer cross-linker is selected from the group consisting of triallylisocyanurate ("TAIC"), triallylcyanurate ("TAC"), and combinations thereof.

20. A method for producing a thermoset article possessing a shape memory comprising:
    irradiating a radiation cross-linkable composition with energy from a radiation source to form a radiation cross-linked composition, the radiation cross-linkable composition comprising
        (a) a copoly(ether-ester-amide) polymer; and
        (b) a monomer cross-linker selected from the group consisting of allylic monomer cross-linkers, methacrylate monomer cross-linkers, acrylate monomer cross-linkers, and combinations thereof;
    heating the radiation cross-linked composition;
    expanding the radiation cross-linked composition; and
    cooling the radiation cross-linked composition to retain a size obtained in the expanding step.

21. The method of claim 20, wherein the polyamide segments of the copoly(ether-ester-amide) polymer consist of polyamide Nylon 12 segments.

22. The method of claim 20, wherein the monomer cross-linker is selected from the group consisting of triallylisocyanurate ("TAIC"), triallylcyanurate ("TAC"), and combinations thereof.

23. A method for forming a wholly or partially encapsulated medical device comprising:
    providing a medical device;
    irradiating a radiation cross-linkable composition with energy from a radiation source to form a radiation cross-linked shaped object, the radiation cross-linkable composition comprising
        (a) a copoly(ether-ester-amide) polymer; and
        (b) a monomer cross-linker selected from the group consisting of allylic monomer cross-linkers, methacrylate monomer cross-linkers, acrylate monomer cross-linkers, and combinations thereof;
    heating the radiation cross-linked shaped object;
    expanding the radiation cross-linked shaped object to a size larger than the medical device;
    cooling the expanded radiation cross-linked shaped object to retain the size obtained in the expanding step;
    placing the medical device within the expanded radiation cross-linked shaped object; and
    heating the expanded radiation cross-linked shaped object to shrink the expanded radiation cross-linked shaped object and thereby wholly or partially encapsulate the medical device.

24. The method of claim 23, wherein the polyamide segments of the copoly(ether-ester-amide) polymer consist of polyamide Nylon 12 segments.

25. The method of claim 23, wherein the monomer cross-linker is selected from the group consisting of triallylisocyanurate ("TAIC"), triallylcyanurate ("TAC"), and combinations thereof.

* * * * *